(12) United States Patent
Sakuragi

(10) Patent No.: US 10,062,184 B2
(45) Date of Patent: Aug. 28, 2018

(54) MEDICAL IMAGE DISPLAY CONTROL DEVICE, METHOD OF OPERATION FOR SAME, AND MEDICAL IMAGE DISPLAY CONTROL PROGRAM

(71) Applicant: FUJIFILM Corporation, Tokyo (JP)

(72) Inventor: Futoshi Sakuragi, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/008,317

(22) Filed: Jan. 27, 2016

(65) Prior Publication Data

US 2016/0140739 A1 May 19, 2016

Related U.S. Application Data

(63) Continuation of application No. PCT/JP2014/003914, filed on Jul. 24, 2014.

(30) Foreign Application Priority Data

Jul. 31, 2013 (JP) ................................. 2013-158591

(51) Int. Cl.
*G06T 11/00* (2006.01)
*A61B 5/00* (2006.01)
(Continued)

(52) U.S. Cl.
CPC ............ *G06T 11/008* (2013.01); *A61B 5/743* (2013.01); *A61B 6/466* (2013.01); *A61B 6/467* (2013.01);
(Continued)

(58) Field of Classification Search
CPC ........... A61B 6/12; A61B 6/505; A61B 6/506; A61B 8/06; A61B 8/08; A61B 6/469;
(Continued)

(56) References Cited

U.S. PATENT DOCUMENTS

2009/0052754 A1* 2/2009 Goto ...................... A61B 5/055
382/128
2011/0245660 A1* 10/2011 Miyamoto ............. A61B 6/032
600/424
2013/0034282 A1* 2/2013 Kaufman .............. G06T 7/0014
382/128

FOREIGN PATENT DOCUMENTS

JP H 09-073557 3/1997
JP 2005-261440 A 9/2005
(Continued)

OTHER PUBLICATIONS

International Search Report (ISR) (PCT Form PCT/ISA/210), in PCT/JP2014/003914, dated Sep. 22, 2014.
(Continued)

*Primary Examiner* — Haixia Du
(74) *Attorney, Agent, or Firm* — McGinn IP Law Group, PLLC.

(57) ABSTRACT

There are provided: a region extraction unit that extracts a plurality of regions from a three-dimensional image of a subject; an internal tissue information acquisition unit that sets, as a crossing region, a region that a light beam used when projecting the three-dimensional image onto the two-dimensional projection plane crosses first among the plurality of regions, sets, as a first intersection, a point on a region crossing the light beam first when the crossing region is excluded, sets, as a second intersection, a point crossing the crossing region when there is an extension in an opposite direction to a traveling direction of the light beam from the first intersection, and acquires information of an internal tissue included between the first and second intersections; and a display control unit that displays the internal tissue information so as to be superimposed on the three-dimensional image.

16 Claims, 4 Drawing Sheets

(51) Int. Cl.
*A61B 6/00* (2006.01)
*G06T 7/00* (2017.01)
*G06T 15/10* (2011.01)
*G06T 15/08* (2011.01)
*G06T 19/00* (2011.01)

(52) U.S. Cl.
CPC ............ *G06T 7/0012* (2013.01); *G06T 15/08* (2013.01); *G06T 15/10* (2013.01); *G06T 19/00* (2013.01); *G06T 2207/10081* (2013.01); *G06T 2207/30088* (2013.01); *G06T 2207/30096* (2013.01); *G06T 2207/30101* (2013.01); *G06T 2210/41* (2013.01)

(58) Field of Classification Search
CPC ......... A61B 6/504; A61B 6/466; A61B 5/489; A61B 2090/367; G06T 15/08; G06T 2207/30004; G06T 2210/41; G06T 7/38; G06T 11/008; G06T 2207/10072; G06T 2207/10081; G06T 2207/10116; G06T 2207/30028; G06T 2207/30061; G06T 2207/30172; G06T 7/11; G06T 2207/30101; G06T 19/00; G06T 2200/04; G06T 15/00; G06T 2207/30016; G06K 2209/05; Y10S 128/922

See application file for complete search history.

(56) References Cited

FOREIGN PATENT DOCUMENTS

| | | |
|---|---|---|
| JP | 2007-325629 A | 12/2007 |
| JP | 2012-085833 A | 5/2012 |
| WO | WO 2008/050823 | 5/2008 |

OTHER PUBLICATIONS

Written Opinion of the International Searching Authority (PCT/ISA/237) and a partial English translation, dated Sep. 22, 2014.
Japanese Office Action in Japanese Application No. 2013-158591, dated Sep. 6, 2016 with an English translation thereof.

* cited by examiner

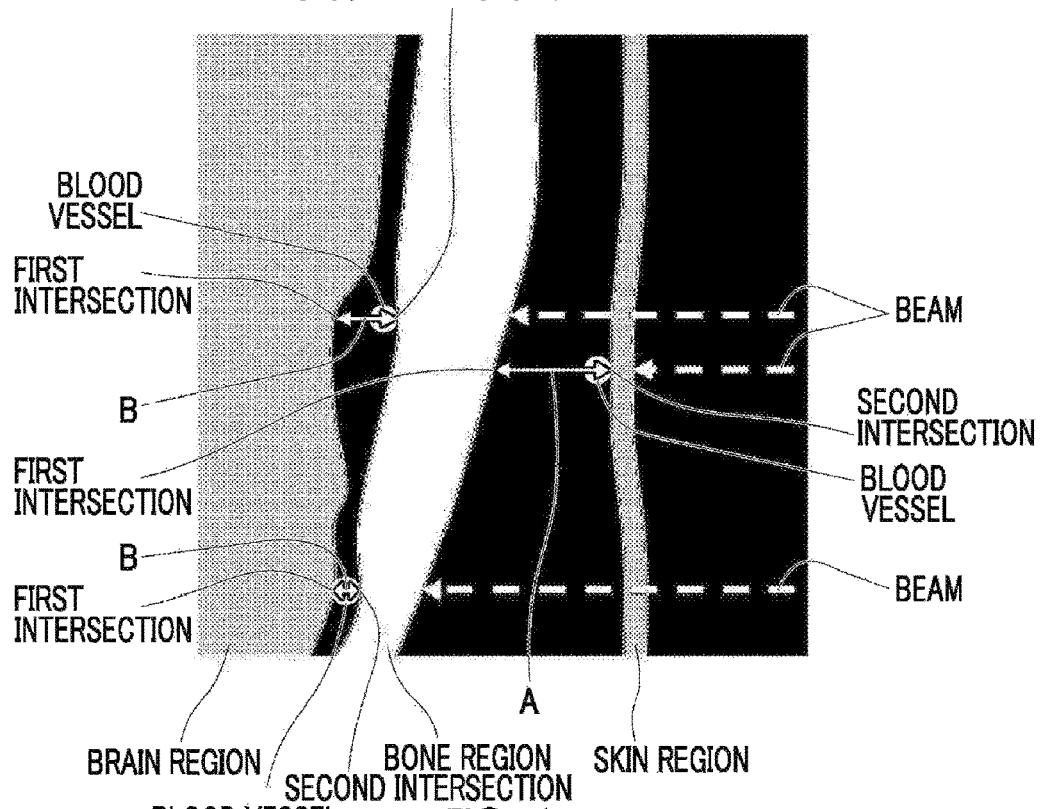
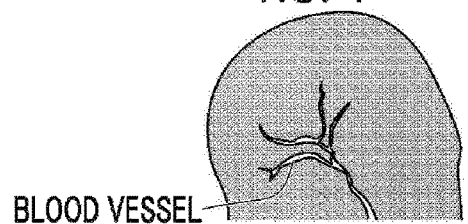
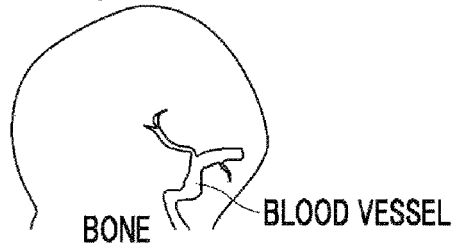

MEDICAL IMAGE DISPLAY CONTROL DEVICE, METHOD OF OPERATION FOR SAME, AND MEDICAL IMAGE DISPLAY CONTROL PROGRAM

CROSS-REFERENCE TO RELATED APPLICATIONS

This application is a Continuation of PCT International Application No. PCT/JP2014/003914 filed on Jul. 24, 2014, which claims priority under 35 U.S.C. § 119 (a) to Japanese Patent Application No. 2013-158591 filed on Jul. 31, 2013. Each of the above application(s) is hereby expressly incorporated by reference, in its entirety, into the present application.

BACKGROUND OF THE INVENTION

1. Field of the Invention

The present invention relates to a medical image display control device, a method of operation for the same, and a medical image display control program for displaying the internal tissue of a subject so as to be superimposed on a three-dimensional image of the subject.

2. Description of the Related Art

In the related art, the planning of actual surgery or the like has been performed using a three-dimensional image captured before surgery. When performing such surgical planning, the internal tissue, such as blood vessels at the back of the skin tissue or the bone tissue, needs to be visualized in some cases.

Specifically, for example, in the case of performing craniotomy, only things on the surface are visible when performing actual surgery since the head has a layer structure of a skin region, a bone region, and a brain region from the surface. Therefore, when incising the skin, blood vessels under the skin are the important tissue for the surgery. In addition, when opening the bone, brain veins or brain arteries under the bone are the important tissue for the surgery.

In such a case, in general, the internal tissue, such as blood vessels, can be displayed by extracting the skin tissue or the bone tissue and adjusting the opacity or the attenuation.

In order to display the internal tissue, JP2007-325629A has proposed to display a three-dimensional image of the internal tissue excluding, for example, a region of the skin tissue by setting a predetermined range from the surface of the subject as a removal layer and constructing a three-dimensional image from which the removal layer has been removed.

SUMMARY OF THE INVENTION

However, in the method of adjusting the opacity or the attenuation of the skin tissue or the bone tissue as described above, there is a problem that the information of the skin surface or the bone surface required for actual surgery is not clear.

In the method disclosed in JP2007-325629A, it is necessary to set the range to be removed from the surface of the subject. However, in the planning of the craniotomy described above, an image may need to be displayed in a state in which a part of the skin is incised so that the bone is visible. When both the skin region and the bone region are displayed simultaneously in this manner, it is very difficult to set the removal ranges of the skin region and the bone region separately in order to display both the blood vessels under the skin region and the blood vessels under the bone region since the thicknesses of the skin region and the bone region are different.

In addition, since the thickness of the bone region differs depending on the location, it is more difficult to set the thickness.

The present invention has been made in view of the above situation, and it is an object of the present invention to provide a medical image display control device, a method of operation for the same, and a medical image display control program that can display an internal tissue under a region, which is currently displayed, so as to be appropriately superimposed on the region without designating a removal range unlike in the related art when displaying the internal tissue of the subject.

A medical image display control device of the present invention includes: a region extraction unit that extracts a plurality of regions, which overlap each other in a viewing direction when projecting a three-dimensional image of a subject onto a two-dimensional projection plane, from the three-dimensional image; an internal tissue information acquisition unit that sets, as a crossing region, a region that a light beam used when projecting the three-dimensional image onto the two-dimensional projection plane crosses first among the plurality of regions, sets, as a first intersection, a point on a region crossing the light beam first when the crossing region is excluded, sets, as a second intersection, a point crossing the crossing region when there is an extension in an opposite direction to a traveling direction of the light beam from the first intersection, and acquires information of an internal tissue included between the first and second intersections; and a display control unit that displays the internal tissue information so as to be superimposed on the three-dimensional image projected onto the two-dimensional projection plane.

In the medical image display control device of the present invention described above, the internal tissue information acquisition unit can detect a specific tissue region from the internal tissue information, and the display control unit can display the specific tissue region so as to be superimposed on the three-dimensional image.

The internal tissue information acquisition unit can detect the specific tissue region by detecting a value within a range set in advance from the internal tissue information.

The internal tissue information acquisition unit can acquire a maximum value, a minimum value, a sum value, an average value, or a volume rendering value of pixels on the light beam between the first and second intersections as the internal tissue information.

The display control unit can perform switching between display and non-display of a three-dimensional image of the plurality of regions.

The region extraction unit can extract at least three regions, the internal tissue information acquisition unit can acquire at least two pieces of the internal tissue information between at least the three regions, and the display control unit can display the at least two pieces of the internal tissue information in different display modes.

The display control unit can display the internal tissue information in a different display mode according to a position between the first and second intersections.

A blood vessel region information can be included in the internal tissue information.

The region extraction unit can extract a skin region, an organ region, or a tumor region.

An operation method of a medical image display control device of the present invention is an operation method of a medical image display control device including a region extraction unit, an internal tissue information acquisition unit, and a display control unit. The method includes: causing the region extraction unit to extract a plurality of regions, which overlap each other in a viewing direction when projecting a three-dimensional image of a subject onto a two-dimensional projection plane, from the three-dimensional image; causing the internal tissue information acquisition unit to set, as a crossing region, a region that a light beam used when projecting the three-dimensional image onto the two-dimensional projection plane crosses first among the plurality of regions, set, as a first intersection, a point on a region crossing the light beam first when the crossing region is excluded, set, as a second intersection, a point crossing the crossing region when there is an extension in an opposite direction to a traveling direction of the light beam from the first intersection, and acquire information of an internal tissue included between the first and second intersections; and causing the display control unit to display the internal tissue information so as to be superimposed on the three-dimensional image projected onto the two-dimensional projection plane.

A medical image display control program of the present invention causes a computer to function as: a region extraction unit that extracts a plurality of regions, which overlap each other in a viewing direction when projecting a three-dimensional image of a subject onto a two-dimensional projection plane, from the three-dimensional image; an internal tissue information acquisition unit that sets, as a crossing region, a region that a light beam used when projecting the three-dimensional image onto the two-dimensional projection plane crosses first among the plurality of regions, sets, as a first intersection, a point on a region crossing the light beam first when the crossing region is excluded, sets, as a second intersection, a point crossing the crossing region when there is an extension in an opposite direction to a traveling direction of the light beam from the first intersection, and acquires information of an internal tissue included between the first and second intersections; and a display control unit that displays the internal tissue information so as to be superimposed on the three-dimensional image projected onto the two-dimensional projection plane.

According to the medical image display control device, the method of operation for the same, and the medical image display control program of the present invention, a plurality of regions overlapping each other in the viewing direction when projecting the three-dimensional image of the subject onto the two-dimensional projection plane are extracted from the three-dimensional image, a region that the light beam used when projecting the three-dimensional image onto the two-dimensional projection plane crosses first among the plurality of regions is set as a crossing region, a point on a region crossing the light beam first when the crossing region is excluded is set as a first intersection, a point crossing the crossing region when there is an extension in the opposite direction to the traveling direction of the light beam from the first intersection is set as a second intersection, and the information of the internal tissue included between the first and second intersections is acquired. Therefore, it is possible to acquire the internal tissue information without a need to designate a removal range unlike in the related art.

In addition, since the internal tissue information is displayed so as to be superimposed on the three-dimensional image projected onto the two-dimensional projection plane, it is possible to appropriately check the state of the surface of the skin or the state of the surface of the bone, for example, in the head surgery planning, without losing the information of the surface of the subject.

BRIEF DESCRIPTION OF THE DRAWINGS

FIG. 3 is a diagram for explaining a method of acquiring internal tissue information.

FIG. 4 is a diagram showing an example in which an image of blood vessels present between a skin region and a bone region is displayed so as to be superimposed on an image of the skin region.

FIG. 5 is a diagram showing an example in which an image of blood vessels present between a bone region and a brain region is displayed so as to be superimposed on an image of the bone region.

DESCRIPTION OF THE PREFERRED EMBODIMENTS

Figure 1:
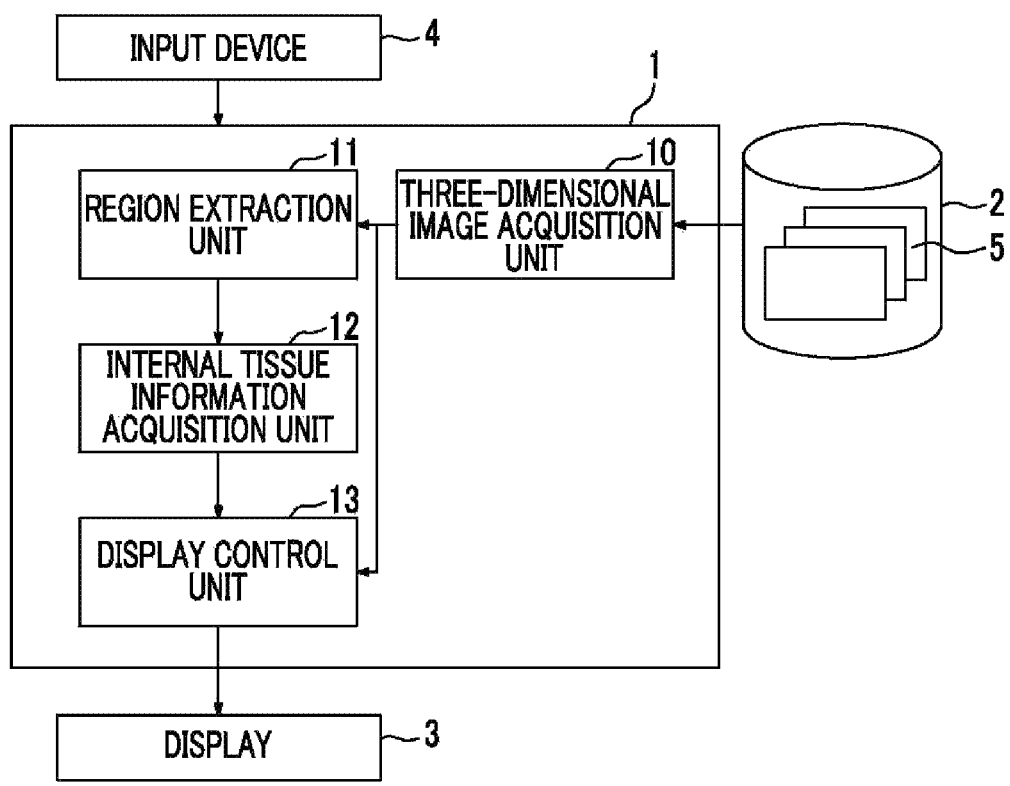
FIG. 1 is a block diagram showing the schematic configuration of a medical image diagnostic support system using an embodiment of a medical image display control device, a method of operation for the same, and a medical image display control program of the present invention.

Hereinafter, a medical image diagnostic support system using an embodiment of a medical image display control device, a method of operation for the same, and a medical image display control program of the present invention will be described in detail with reference to the diagrams. FIG. 1 is a block diagram showing the schematic configuration of a medical image diagnostic support system of the present embodiment.

As shown in FIG. 1, the medical image diagnostic support system of the present embodiment includes a medical image display control device 1, a three-dimensional image storage server 2, a display 3, and an input device 4.

The medical image display control device 1 is realized by installing a medical image display control program of the present embodiment on a computer. The medical image display control device 1 includes one or more central processing units (CPU) and semiconductor memories or one or more storage devices, such as hard disks or solid state drives (SSD). The medical image display control program of the present embodiment is installed on the storage device, and the central processing unit executes the medical image display control program to operate a three-dimensional image acquisition unit 10, a region extraction unit 11, an internal tissue information acquisition unit 12, and a display control unit 13 as shown in FIG. 1. A medical image display control program recorded on a recording medium, such as a CD-ROM, may be used, or a medical image display control program that is provided by Software as a Service (SaaS) through the Internet may be used.

The three-dimensional image acquisition unit 10 acquires a three-dimensional image 5 of the subject captured in advance before surgery, examination, or the like. Examples of the three-dimensional image 5 include volume data reconstructed from slice data, which is output from a CT apparatus or a magnetic resonance imaging (MRI) apparatus, and volume data output from a multi-slice (MS) CT apparatus or a cone beam CT apparatus. The three-dimensional image 5 is stored in the three-dimensional image storage server 2 in advance together with the identification information of the subject, and the three-dimensional image acquisition unit 10 reads the three-dimensional image 5 corresponding to the identification information of the subject, which is input through the input device 4, from the three-dimensional image storage server 2. In addition, the three-dimensional image acquisition unit 10 may acquire a number of pieces of slice data to generate volume data.

The three-dimensional image storage server 2 may be a so-called single server device, or may be configured to store a three-dimensional image in a server device connected to a so-called cloud.

In the present embodiment, it is assumed that the three-dimensional image acquisition unit 10 acquires a three-dimensional image of the head. It is also possible to acquire a three-dimensional image of the chest including a heart region, the abdomen including a liver region or a bone region, or the like without being limited to the head.

The three-dimensional image 5 acquired by the three-dimensional image acquisition unit 10 is input to the region extraction unit 11, and the region extraction unit 11 extracts a plurality of regions based on the input three-dimensional image 5. Specifically, the three-dimensional image 5 of the head is input to the region extraction unit 11 of the present embodiment, and the region extraction unit 11 extracts a skin region, a bone region, and a brain region of the head based on the input three-dimensional image 5 of the head. The skin region, the bone region, and the brain region are regions overlapping each other in the viewing direction when projecting the three-dimensional image of the head onto the two-dimensional projection plane.

As a method of extracting the skin region, the bone region, and the brain region, the skin region, the bone region, and the brain region may be automatically extracted based on the pixel data of the three-dimensional image 5 of the head using a known method. Alternatively, the user may extract the skin region, the bone region, and the brain region by manually designating each region using the input device 4.

The internal tissue information acquisition unit 12 acquires, as internal tissue information, information of a region interposed between the respective regions extracted by the region extraction unit 11. Specifically, in the present embodiment, information of blood vessels present between the skin region and the bone region and the information of blood vessels present between the bone region and the brain region are acquired as the internal tissue information. The internal tissue information acquisition unit 12 outputs the acquired internal tissue information to the display control unit 13. The method of acquiring the internal tissue information will be described in detail later.

The display control unit 13 displays, on the display 3, the three-dimensional image 5 of the head acquired by the three-dimensional image acquisition unit 10, for example, a projection image that is projected on the two-dimensional projection plane using a volume rendering method, a surface rendering method, or the like. In this case, the display control unit 13 of the present embodiment displays the internal tissue information so as to be superimposed on the projection image. Specifically, the display control unit 13 of the present embodiment displays an image of blood vessels between the skin region and the bone region so as to be superimposed on the projection image of the skin region of the head, or displays an image of blood vessels between the bone region and the brain region so as to be superimposed on the projection image of the bone region of the head. As a method of superposition display, the projection image and the image of internal tissues may be alpha blended, or addition display for overlaying the image of internal tissues on the projection image is possible.

The input device 4 includes a mouse, a keyboard, and the like, and receives an operation input from the user. In particular, the input device 4 of the present embodiment receives a setting input of the beam direction used when projecting the three-dimensional image 5 of the head onto the two-dimensional projection plane, or receives a setting input of a display target displayed on the display 3. As a display target, for example, the skin region of the head and blood vessels between the skin region and the bone region are set and input, or the bone region of the head and blood vessels between the bone region and the brain region are set and input.

Figure 2:
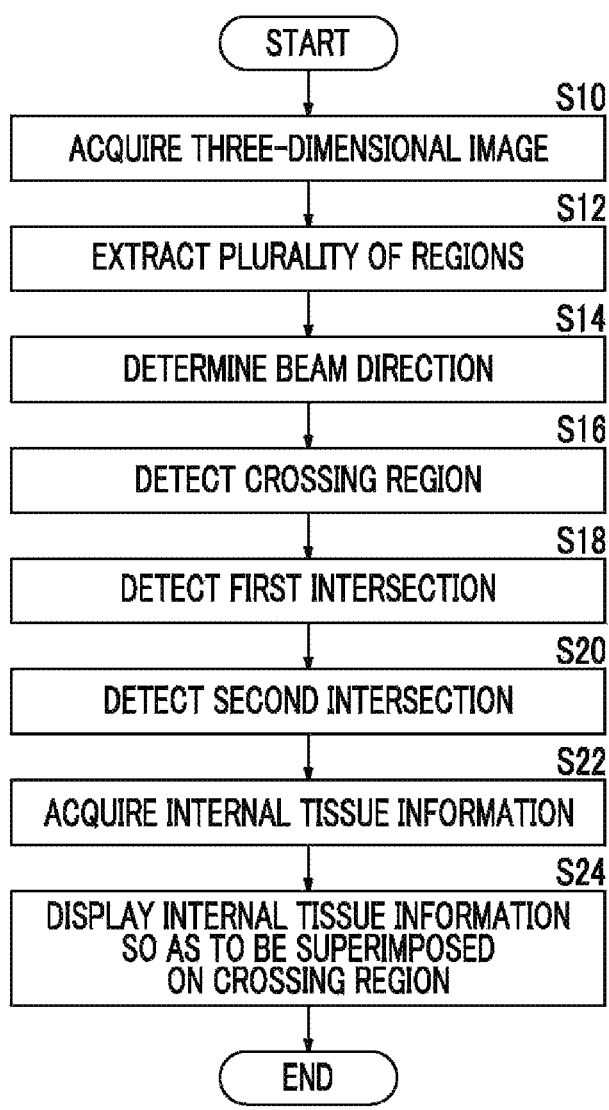
FIG. 2 is a flowchart for explaining the operation of the medical image diagnostic support system shown in FIG. 1.

Next, the operation of the medical image diagnostic support system of the present embodiment will be described with reference to the flowchart shown in FIG. 2.

First, the user inputs the identification information of the subject using the input device 4, and the three-dimensional image acquisition unit 10 of the medical image display control device 1 reads and acquires the three-dimensional image 5 corresponding to the input identification information of the subject from the three-dimensional image storage server 2 (S10).

The three-dimensional image 5 acquired by the three-dimensional image acquisition unit 10 is input to the region extraction unit 11, and the region extraction unit 11 extracts a plurality of regions based on the input three-dimensional image 5 (S12). Specifically, the region extraction unit 11 in the present embodiment extracts a skin region, a bone region, and a brain region of the head shown in FIG. 3 based on the three-dimensional image 5 of the head.

Then, the user sets and inputs a beam direction, which is used when projecting the three-dimensional image 5 of the head onto the two-dimensional projection plane, using the input device 4 (S14). When projecting the three-dimensional image 5 onto the two-dimensional projection plane using a parallel projection method, a direction perpendicular to the two-dimensional projection plane is set as the beam direction. In addition, when projecting a three-dimensional image onto the two-dimensional projection plane using a perspective projection method, a linear direction from a predetermined starting point to each pixel of the two-dimensional projection plane is set as the beam direction.

In the present embodiment, it is assumed that the beam direction shown by the dashed arrow in FIG. 3 is set and input. The dashed arrow direction is the beam direction. Although only three light beams are shown in FIG. 3, it is assumed that a number of light beams in a pixel unit are set.

In this case, the user also inputs the information of the display target using the input device 4. Here, a scene of incising the skin of the head is assumed, and the skin of the head and blood vessels between the skin and the bone are assumed to be set and input as display targets.

Then, information of the skin region, the bone region, and the brain region extracted by the region extraction unit 11 is input to the internal tissue information acquisition unit 12, and the internal tissue information acquisition unit 12 acquires information of the blood vessels present between the skin region and the bone region based on the information on these regions and the information of the beam direction set by the user.

Specifically, first, a region that each light beam crosses first is detected and set as a crossing region (S16). In the present embodiment, the skin region shown in FIG. 3 is set as a crossing region.

As a crossing region detection method, a region that each light beam crosses first may be detected from each light beam and the coordinates values of each region, or a detection method may be determined according to the three-dimensional image display method. Specifically, for example, when displaying a three-dimensional image by volume rendering, a point when the sum value of the opacity along the beam direction exceeds a predetermined threshold value may be set as an intersection, and a region including the intersection may be detected as a crossing region. In addition, when displaying a three-dimensional image by surface rendering, an intersection between the beam direction and the surface may be set as an intersection, and a region including the intersection may be detected as a crossing region.

Then, when the skin region (crossing region) is excluded, a point on a region crossing each light beam first is detected and set as a first intersection (S18). In the present embodiment, a point on the bone region crossing each light beam first as shown in FIG. 3 is set as the first intersection.

Then, a point crossing the crossing region when there is an extension in an opposite direction to the traveling direction of light from the first intersection is detected and set as the second intersection (S20). In the present embodiment, a second intersection on the skin region shown in FIG. 3 is set.

Then, the internal tissue information acquisition unit 12 acquires information included in a region between the first and second intersections, which have been set as described above, as internal tissue information (S22). In the present embodiment, pixels of the blood vessels between the skin region and the bone region are detected by detecting pixels having values within a range set in advance among pixels in the range shown by arrow A in FIG. 3. The range set in advance is set according to the type of blood vessel contrast medium. The detection range of internal tissue information may not necessarily be the entire range between the first and second intersections, and may be a range of a distance set in advance from the second intersection.

The blood vessel information detected by the internal tissue information acquisition unit 12 is input in the display control unit 13. Then, the display control unit 13 displays a blood vessel image on the display 3 based on the input blood vessel information so as to be superimposed on a projection image, which is obtained by projecting the three-dimensional image 5 onto the two-dimensional projection plane (S24). Since the skin and the blood vessels between the skin and the bone are set and input as display targets herein, an image shown in FIG. 4 is displayed on the display 3.

Although the case in which the skin of the head and the blood vessels between the skin and the bone are set and input as display targets has been described above, the bone of the head and the blood vessels between the bone and the brain may be set and input as display targets.

In this case, the internal tissue information acquisition unit 12 acquires internal tissue information in a state in which a skin region is excluded.

Specifically, in this case, a bone region is detected and set as a crossing region that each light beam crosses first. Then, when the bone region is excluded, a point on the brain region that crosses each light beam first is detected and set as the first intersection.

Then, a point crossing the bone region when there is an extension in an opposite direction to the traveling direction of light from the first intersection on the brain region is detected and set as the second intersection.

Then, the internal tissue information acquisition unit 12 acquires information included between the first and second intersections, which have been set as described above, as internal tissue information. Specifically, pixels of the blood vessels between the bone region and the brain region are detected by detecting pixels, which have values within a range set in advance, among pixels in the range shown by arrow B in FIG. 3.

The blood vessel information detected by the internal tissue information acquisition unit 12 is input to the display control unit 13, and the display control unit 13 displays an image, in which the blood vessel image is superimposed on the image of the bone, on the display 3 as shown in FIG. 5.

Figure 6:
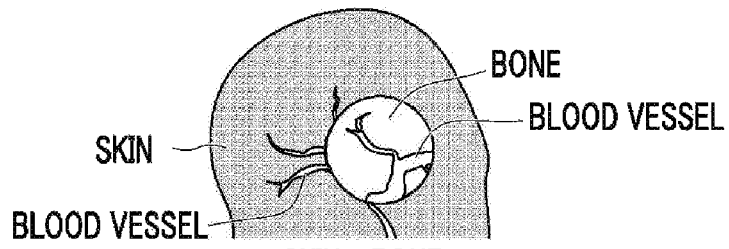
FIG. 6 is a diagram showing an example in which an image of blood vessels is displayed so as to be superimposed on each of an image of a bone region and an image of a skin region.

In addition, it is also possible to designate a display target assuming a state in which a part of the skin of the head is incised. In this case, for example, an image shown in FIG. 6 is displayed on the display 3. A method of acquiring the information of the blood vessel superimposed on the image of the skin and the information of the blood vessel superimposed on the image of the bone is the same as described above. In addition, as shown in FIG. 6, when the information of a plurality of internal tissues between different regions is acquired and displayed, the information of the plurality of internal tissues may also be displayed in different display modes. Specifically, for example, in FIG. 6, the blood vessel image superimposed on the image of the skin may be displayed in red, and the blood vessel image superimposed on the image of the bone may be displayed in blue. Therefore, it is possible to make it clear that these are images of different blood vessels.

In addition, the display control unit 13 may perform switching between the display and non-display of the image of the skin region or the bone region shown in FIGS. 4 to 6, for example, in response to an instruction from the user using the input device 4.

For the images of the blood vessels shown in FIGS. 4 to 6, the display control unit 13 may display the blood vessels in different display modes according to a position between the first and second intersections. Specifically, for example, blood vessels between the skin region and the bone region shown in FIG. 3 may be displayed in different colors or different brightnesses according to the distance from the skin region or the bone region. Similarly, blood vessels between the bone region and the brain region shown in FIG. 3 may be displayed in different colors or different brightnesses according to the distance from the bone region and the brain region. By performing such a display, it is possible to check how far from the skin region or the bone region the blood vessel is located. This is useful when cutting the skin and the bone.

In the above explanation of the embodiment, the three-dimensional image of the head is acquired, the skin region, the bone region, and the brain region of the head are extracted, and the information of blood vessels between these regions is acquired as internal tissue information. However, the internal tissue information is not limited to this.

Figure 7:
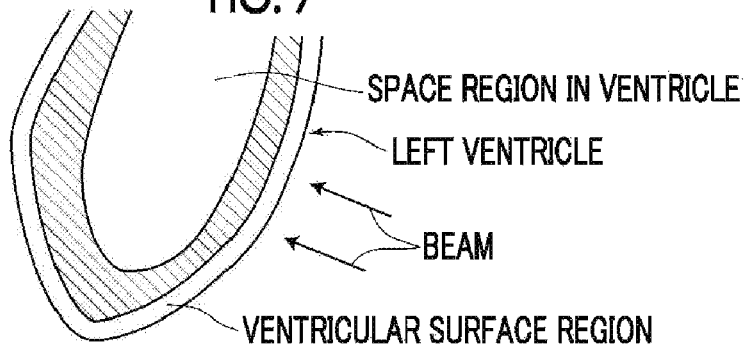
FIG. 7 is a diagram for explaining an example of acquiring the information of the myocardium between the surface region of the left ventricle and the space region in the ventricle as internal tissue information.

For example, a three-dimensional image of the left ventricle of the heart shown in FIG. 7 may be acquired, a ventricular surface region of the left ventricle and a space region in the ventricle may be extracted as regions overlapping each other in the viewing direction, information of the myocardium between these regions (in the shaded range shown in FIG. 7) may be acquired as internal tissue information, and an image in which the information of the myocardium is superimposed on the projection image of the left ventricle may be displayed. For the ventricular surface region, it is preferable that a range from the surface of the ventricle to a depth set in advance is set as the ventricle surface region. The method of acquiring the internal tissue information is the same as described above.

Figure 8:
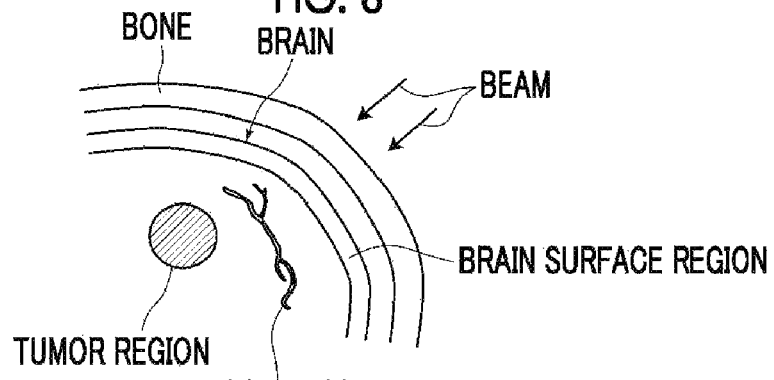
FIG. 8 is a diagram for explaining an example of acquiring the information of blood vessels between a surface region and a tumor region of the brain as internal tissue information.

In addition, a case may be assumed in which surgery to remove a tumor formed in the brain of the head is performed. In this case, as shown in FIG. 8, a surface region and a tumor region may be extracted as regions overlapping each other in the viewing direction, information of blood vessels between these regions may be acquired as internal tissue information, and an image in which a blood vessel image is superimposed on a projection image of the brain may be displayed. For the brain surface region, it is preferable that a range from the surface of the brain to a depth set in advance is set as the brain surface region. The method of acquiring the internal tissue information is the same as described above.

Figure 9:
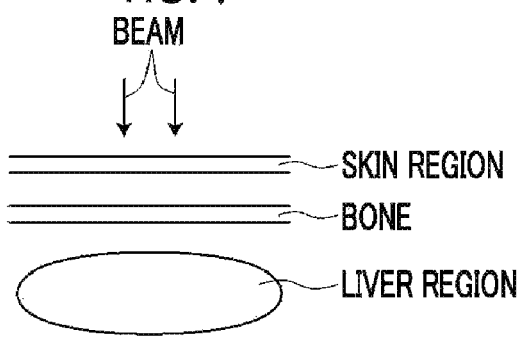
FIG. 9 is a diagram for explaining an example of acquiring the information of a bone between a skin region and a liver region as internal tissue information.

In addition, a case may be assumed in which an endoscope is inserted into the abdomen to perform liver surgery. In this case, a skin region and a liver region may be extracted as regions overlapping each other in the viewing direction from a three-dimensional image of the abdomen including the liver region as shown in FIG. 9, information of the bone between these regions may be acquired as internal tissue information, and an image in which an image of the bone is superimposed on a projection image of the skin may be displayed. The method of acquiring the internal tissue information is the same as described above.

In the embodiment described above, the internal tissue information is acquired by detecting pixels having values within a range set in advance among pixels in the range between the first and second intersections. However, the present invention is not limited to this, and the maximum value, the minimum value, the sum value, the average value, or the volume rendering value of pixels on the light beam between the first and second intersections may be acquired as internal tissue information.

What is claimed is:

1. A medical image display control device, comprising:
a memory; and
a processor that is connected to the memory, wherein the processor is configured to:
extract a plurality of regions, which overlap each other in a viewing direction when projecting a three-dimensional image of a subject onto a two-dimensional projection plane, from the three-dimensional image of the subject;
set, as a crossing region, a region that a light beam used when projecting the three-dimensional image of the subject onto the two-dimensional projection plane crosses first among the plurality of regions, set, as a first intersection, a point on a region crossing the light beam first when the crossing region is excluded, set, as a second intersection, a point crossing the crossing region when there is an extension in an opposite direction to a traveling direction of the light beam from the first intersection, and acquire internal tissue information of an internal tissue included between the first and second intersections;
display the internal tissue information on a display unit so as to be superimposed on a part of the three-dimensional image corresponding to the crossing region projected onto the two-dimensional projection plane;
extract at least three regions of the plurality of regions;
acquire at least two pieces of the internal tissue information between at least the three regions: and
display the at least two pieces of the internal tissue information that are superimposed on different three dimensional images expressing different areas in different display modes.

2. The medical image display control device according to claim 1, wherein the processor is further configured to detect a specific tissue region from the internal tissue information, and
wherein the processor is further configured to display the specific tissue region so as to be superimposed on the part of the three-dimensional image corresponding to the crossing region.

3. The medical image display control device according to claim 2, wherein the processor is further configured to detect the specific tissue region by detecting a value within a range set in advance from the internal tissue information.

4. The medical image display control device according to claim 1, wherein the processor is further configured to acquire a maximum value, a minimum value, a sum value, an average value, or a volume rendering value of pixels on the light beam between the first and second intersections as the internal tissue information.

5. The medical image display control device according to claim 1, wherein the processor is further configured to perform switching between display and non-display of a three-dimensional image of the plurality of regions.

6. The medical image display control device according to claim 1, wherein the processor is further configured to display the internal tissue information in a different display mode according to a position between the first and second intersections.

7. The medical image display control device according to claim 1, wherein a blood vessel region information is included in the internal tissue information.

8. The medical image display control device according to claim 1, wherein the processor is further configured to extract one of:
a skin region;
an organ region;
a tumor region, as one of the plurality of regions.

9. The medical image display control device according to claim 1, wherein the processor is further configured to extract the plurality of regions, the plurality of regions comprising a bone region.

10. The medical image display control device according to claim 1, wherein the processor is further configured to detect a specific tissue region from the internal tissue information.

11. The medical image display control device according to claim 1, wherein the processor is further configured to display a specific tissue region so as to be superimposed on the three-dimensional image.

12. The medical image display control device according to claim 1, wherein the processor is further configured to detect a specific tissue region by detecting a value within a range set in advance from the internal tissue information.

13. The medical image display control device according to claim 1, wherein the at least two pieces of the internal tissue information include a blood vessel image superimposed on an image of a skin and the blood vessel image superimposed on an image of a bone.

14. The medical image display control device according to claim 13, wherein the blood vessel image superimposed on the image of the skin is displayed in a different color than the blood vessel image superimposed on the image of the bone.

15. An operation method of a medical image display control device including a region extraction unit that extracts a plurality of regions, which overlap each other in a viewing direction when projecting a three-dimensional image of a subject onto a two-dimensional projection plane, from the three-dimensional image, the method, being performed by a processor, comprising:
- extracting a plurality of regions, which overlap each other in a viewing direction when projecting a three-dimensional image;
- setting, as a crossing region, a region that a light beam used when projecting the three-dimensional image onto the two-dimensional projection plane crosses first among the plurality of regions, setting, as a first intersection, a point on a region crossing the light beam first when the crossing region is excluded, setting, as a second intersection, a point crossing the crossing region when there is an extension in an opposite direction to a traveling direction of the light beam from the first intersection, and acquiring internal tissue information of an internal tissue included between the first and second intersections;
- displaying the internal tissue information so as to be superimposed on a part of the three-dimensional image corresponding to the crossing region projected onto the two-dimensional projection plane;
- extracting at least three regions of the plurality of regions;
- acquiring at least two pieces of the internal tissue information between at least the three regions; and
- displaying the at least two pieces of the internal tissue information that are superimposed on different three dimensional images expressing different areas in different display modes.

16. A non-transitory computer-readable recording medium having stored therein a medical image display control program causing a computer to perform a processing, the processing comprising:
- extracting a plurality of regions, which overlap each other in a viewing direction when projecting a three-dimensional image of a subject onto a two-dimensional projection plane, from the three-dimensional image of the subject;
- setting, as a crossing region, a region that a light beam used when projecting the three-dimensional image of the subject onto the two-dimensional projection plane crosses first among the plurality of regions, setting, as a first intersection, a point on a region crossing the light beam first when the crossing region is excluded, sets, as a second intersection, a point crossing the crossing region when there is an extension in an opposite direction to a traveling direction of the light beam from the first intersection, and acquiring internal tissue information of an internal tissue included between the first and second intersections;
- displaying the internal tissue information on a display unit so as to be superimposed on a part of the three-dimensional image corresponding to the crossing region projected onto the two-dimensional projection plane;
- extracting at least three regions of the plurality of regions;
- acquiring at least two pieces of the internal tissue information between at least the three regions; and
- displaying the at least two pieces of the internal tissue information that are superimposed on different three dimensional images expressing different areas in different display modes.

* * * * *